United States Patent [19]
Frey et al.

[11] Patent Number: 4,793,335
[45] Date of Patent: Dec. 27, 1988

[54] BONE IMPLANT FOR FIXING ARTIFICIAL TENDONS OR LIGAMENTS WITH APPLICATION AND EXTRACTION MEANS

[75] Inventors: Otto Frey, Winterthur; Rudolf Koch, Berlingen, both of Switzerland

[73] Assignee: Sulzer Brothers Limited, Winterthur, Switzerland

[21] Appl. No.: 5,469

[22] Filed: Jan. 20, 1987

[30] Foreign Application Priority Data

Jan. 28, 1986 [CH] Switzerland ............... 320/86

[51] Int. Cl.$^4$ .............. A61F 5/04; A61B 17/04; A61B 17/08; A61B 17/18
[52] U.S. Cl. ............... 128/92 R; 128/92 YC; 128/92 VT; 128/334 R; 128/334 C; 623/13; 411/457; 411/469
[58] Field of Search ......... 128/334 R, 334 C, 92 VP, 128/92 YL, 92 YF, 92 YE, 92 YC, 92 YV, 92 VT, 303 R, 92 R; 623/13; 248/205.4, 500, 505, 507, 508, 510; 411/457, 469, 475

[56] References Cited

U.S. PATENT DOCUMENTS

| | | | |
|---|---|---|---|
| 2,418,539 | 4/1947 | Anderson | 411/457 X |
| 4,047,524 | 9/1977 | Hall | 128/92 YF X |
| 4,060,089 | 11/1977 | Noiles | 128/334 C X |
| 4,263,903 | 4/1981 | Griggs | 128/92 YC X |
| 4,278,091 | 7/1981 | Borzone | 128/334 C |
| 4,454,875 | 6/1984 | Pratt et al. | 128/92 YC |
| 4,488,543 | 12/1984 | Tornier | 128/92 YV |
| 4,505,273 | 3/1985 | Braun et al. | 128/334 R X |
| 4,570,623 | 2/1986 | Ellison et al. | 128/334 R X |

Primary Examiner—Richard J. Apley
Assistant Examiner—David J. Bender
Attorney, Agent, or Firm—Kenyon & Kenyon

[57] ABSTRACT

The agraffe is composed of a deformable metal plate having two projections, each of which is provided with a threaded eyelet. In addition, anchored pins are threaded into the respective eyelets and can be selected from a set of pins having different lengths. The deformable plate is arched between the projections and has a plurality of tacks fixably secured in place to increase adhesion of a ligament or tendon to a bone. The instrument for implanting or extracting the agraffe includes a pair of angular sector-shaped grooves of T-shaped cross-sections which are sized to engage with and under the heads of the pins in order to form a connection between the instrument and agraffe.

9 Claims, 3 Drawing Sheets

BONE IMPLANT FOR FIXING ARTIFICIAL TENDONS OR LIGAMENTS WITH APPLICATION AND EXTRACTION MEANS

This invention relates to a bone implant for fixing artificial tendons or ligaments as well as an application and extraction means therefore. More particularly, this invention relates to a surgical agraffe for fixing artifical ligaments and tendons to a bone.

Heretofore, various types of agraffes have been known for the fixing of artificial ligaments and tendons to a bone. For example, U.S. Pat. No. 4,263,903 describes an agraffe which consists of a narrow bridge piece which is bent at the ends at an angle to form two spike-like anchor pins. When fixing an artificial ligament or tendon, the pins are driven into a bone with the bridge piece clamping the ligament or tendon to the bone. However, the clamping effect is achieved only over a relatively narrow width of the bridge-piece. Further, since the anchor pins and bridge-piece form an integral unit, for different "depths" of penetration of the pins into the bone, a number of individual agraffes are required which differ only in the length of the anchored pins. Consequently, if an operating surgeon is to be given a sufficient supply of agraffes with different bridge lengths and widths as well as different pin lengths for each of these lengths and widths, a large assortment will result. This, in turn, complicates manufacture and stock-keeping while also involving great expense.

Accordingly, it is an object to provide an agraffe with which a tendon or ligament may be held over a relatively large area.

It is another object of the invention to provide an agraffe construction which reduces the number of components required for manufacture and inventory purposes.

It is another object of the invention to provide a relatively simple agraffe construction which permits adaptation to different size requirements.

Briefly, the invention provides a surgical agraffe for fixing artifical ligaments and tendons to a bone in which the agraffe comprises a permanently deformable metal plate defining a connecting bridge element and a pair of projections which extend from opposite sides of the bridge element. In addition, the agraffe or staple has a pair of spike-like anchor pins each of which is detachably secured to and which extends from a respective projection.

The permanently deformable metal plate offers a clamping effect which can be distributed over a large area instead of a line type clamping of a ligament. Moreover, the permanent deformability of the plate permits adaptation of the surface area of the plate to the individual bone which is to receive the agraffe.

By using detachably secured anchored pins, the proper length of pin can be selected from an assortment of pins of different lengths, for example, according to an X-ray picture from which the bone thickness can be determined. Further, the pins may be attached to the metal plate prior to sterilization of the agraffe. In this way, the assortment of plate sizes and pin lengths for a complete set of agraffes can be kept relatively small.

In accordance with the invention, each projection of the plate includes a hollow threaded eyelet while each pin is threaded into a respective eyelet. Each pin is also provided with a head which projects from the projection of a plate in knob-like manner. In this respect, the protruding heads can serve for the engagement of a driving or extracting instrument.

The invention also provides a driving and/or extracting instrument having a shank with an enlarged end and a pair of annular sector-shaped grooves of T-shaped cross-section in the end. In addition, each groove is sized to slideably receive a head of a respective pin in order to connect the instrument to the agraffe. Further, each groove may have a circumferentially inclined base for wedging against a head of a pin in order to fixably connect the instrument to the agraffe. Alternatively, any other suitable means may be provided to fixably connect the instrument to an agraffe. For example, clamping screws may be used to fix the heads of the anchor pins of the agraffe in the instrument.

The bridge element may also be arched between a projection relative to a common bearing plane of the projections while a plurality of tacks are secured to and extend from the bridge element to a length of at least one-third the length of the anchor pins beyond the common bearing plane. Such tacks also penetrate into the bone to provide for an increased adhesion of the ligament or tendon since the tacks function as additional anchors which traverse the tendon or ligament to be held.

These and other objects and advantages of the invention will become more apparent from the following detailed description taken in conjunction with the accompanying drawings wherein.

Figure 1:
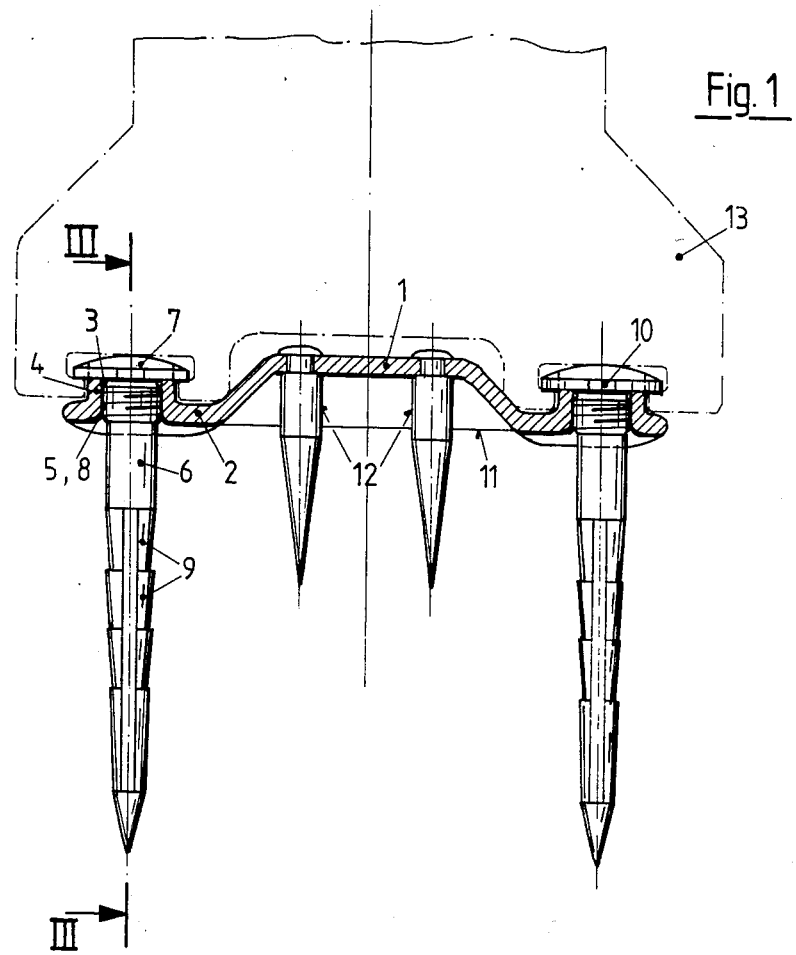
FIG. 1 illustrates a partial cross-sectional view of a surgical agraffe constructed in accordance with the invention.
Figure 2:
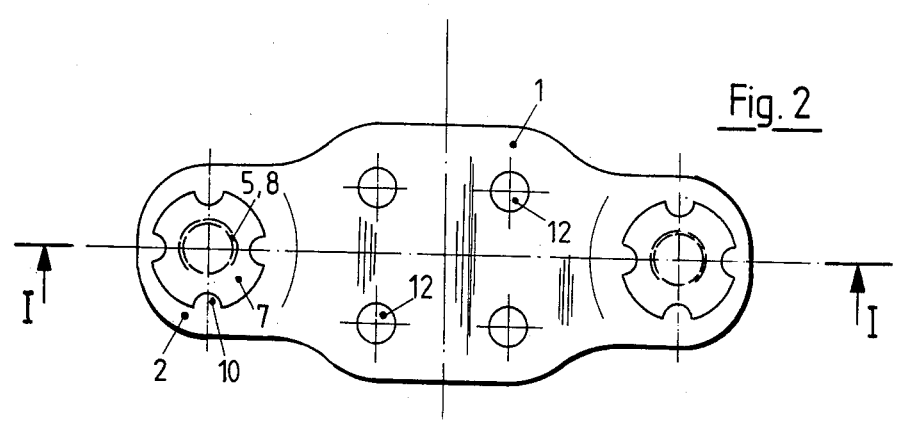
FIG. 2 illustrates a top view of the agraffe of FIG. 1.

Referring to FIGS. 1 and 2, the surgical agraffe includes a permanently deformable metal plate 1 defining a connecting bridge element of substantially square shape and a pair of projections 2 which extend from opposite sides of the bridge element. As indicated, each projection 2 is of fishplate type shape and each has an eyelet 3 which is surrounded by an upstanding wall or lip 4 in which a thread 5 is cut.

Figure 3:
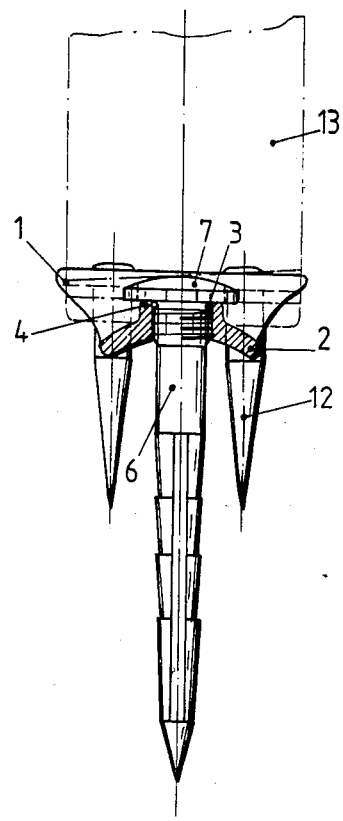
FIG. 3 illustrates a view taken on line III—III of FIG. 1.

As indicated in FIG. 3, the flanks of the projections 2 are permanently deformable for adaptation to an individual bone and are bent slightly downwardly so as to hug, for example, the curvature of a tubular bone (not shown).

Referring to FIG. 1, the surgical agraffe also includes a pair of spike-like anchor pins 6. As indicated, each pin 6 is detachably secured via suitable means to and extends from a respective projection 2. To this end, each pin 6 has a thread 8 which is threaded into the thread 5 of an eyelet 3. In addition, each pin 6 has a head 7 which projects from the projection 2 in knob-like manner. As shown in FIG. 1, the thread 8 of each pin 6 is directly under the head 7 of the pin 6.

Each anchor pin 6 is in the form of a long spike which, in the extracting direction, has a barb-like structure 9. Also, each head 7 is provided with a plurality, i.e., four, cut-outs 10 for a fixing of a tool 13.

Referring to FIG. 1, the bridge element is arched between the projections 2 relative to a common bearing plane 11 of the projections 2, i.e. to the undersides of the vertex region of each projection 2. This arching serves to receive an artificial ligament or tendon (now shown). In addition, a plurality of tacks 12 are fixably secured to and extend from the bridge element. Each tack 12 is of a length so as to extend beyond the common bearing plane 11 by at least one-third the length of the anchor pins 6 beyond the bearing plane 11.

Figure 6:
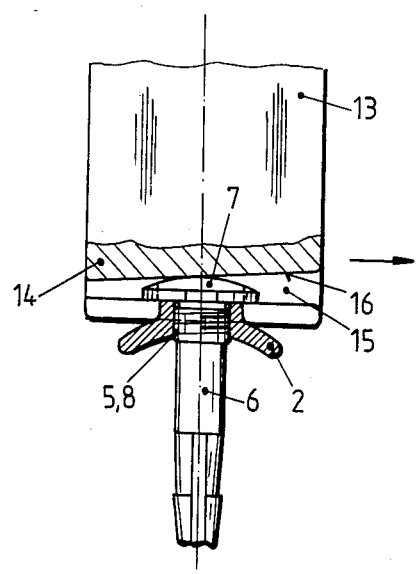
FIG. 6 illustrates a part cross-sectional view of an anchor pin against an inclined base of a groove of the driving and extracting instrument.
Figure 4:
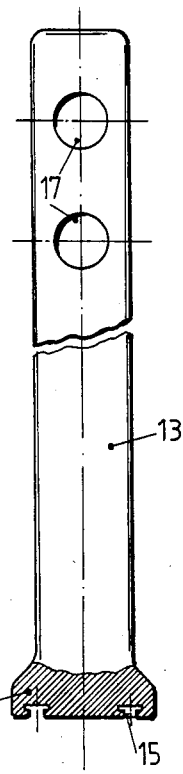
FIG. 4 illustrates a partial cross-sectional view of a driving and extracting instrument in accordance with the invention.
Figure 5:
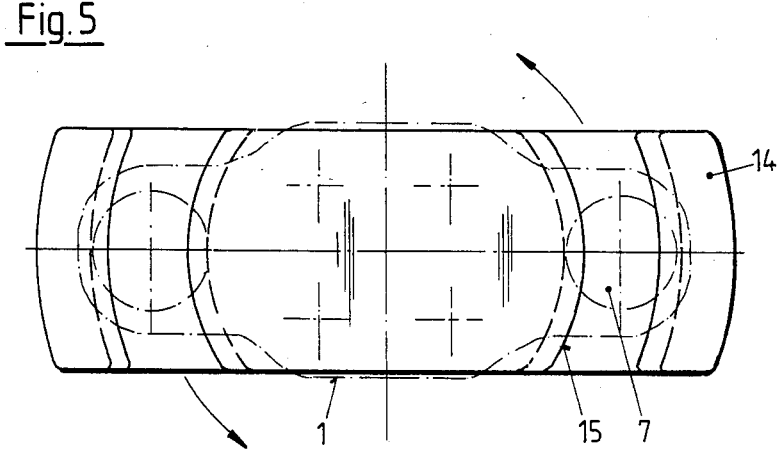
FIG. 5 illustrates a bottom view of the instrument of FIG. 4 to an enlarged scale.

Referring to FIGS. 4 and 5, the driving and extracting instrument 13 by which the agraffe is fixable for its "assembly" and "disassembly" in/from a bone includes a ram type shank which has an enlarged end 14 in which a pair of annular sector-shaped grooves 15 of T-shaped cross-sections are formed (see FIG. 5). Each groove 15 is sized to slidably receive a head 7 of a respective anchor pin 6, as shown in FIG. 1, in order to connect the instrument 13 to the agraffe. To this end, the grooves 15 have the same spacing as the anchor pins 6 of the agraffe. Referring to FIG. 6, each groove 15 of the instrument 13 also has a circumferentially inclined base 16 for wedging against a head 7 of a respective anchor pin 6 in order to fixably connect the instrument 13 to the agraffe. Thus, during rotation of the instrument 13 relative to the heads 7 on the agraffe as indicated by the arrow in FIG. 6, the heads 7 become wedged within the grooves 15. Alternatively, other means of fixation between the instrument 13 and the agraffe are possible, for example, clamping of the agraffe by means of a clamping screw (not shown).

In order to drive an agraffe into a bone, the instrument 13 is engaged with the heads 7 of the pins 6 of the agraffe and a suitable hammer or the like is struck against the upper end of the shank 13 to drive the pins 6 into the bone while clamping against the ligament or tendon. In order to remove an agraffe from a bone, the instrument 13 is provided with a plurality of bores 17 in the upper region through which transverse rods may be inserted. Subsequent hammering or tapping against such rods from below serve to pull the agraffe from the bone.

The invention thus provides an agraffe which can be adapted to the surgical procedure being contemplated. To this end, after determining the length of anchoring pins which are to be used, the appropriate pair of anchor pins can be selected from a set of pins of different lengths and then threaded into the metal plate. The thus completed agraffe can then be sterilized using known techniques and presented to a surgeon for implanting in a bone.

In similar manner, the size of the deformable plate may be selected independently of the length of the pins. In this way, relatively wide plates can be selected to increase the clamping effect on a ligament or tendon being secured in place or vice versa.

The invention further reduces the need to inventory a large number of components in order to provide appropriately sized agraffes for afixation of ligaments and tendons.

What is claimed is:

1. A bone implant for fixing artificial ligaments and tendons to a bone, said implant comprising;
    a permanently deformable metal plate defining a connecting bridge element and a pair of projections extending from opposite sides of said bridge element;
    a pair of spike-like anchor pins, each said pin extending from a respective projection; and
    means between each said projection and each said pin for detachably securing each said pin to a respective projection for selective removal therefrom to adapt to a bone thickness for fixation of an artificial ligament.

2. A bone implant as set forth in claim 1 wherein said means includes a threaded eyelet in a respective projection and a thread on a respective pin.

3. A bone implant as set forth in claim 1 further comprising a plurality of tacks secured to and extending from said bridge element.

4. In combination,
    at least one bone implant having a permanently deformable metal plate and a pair of spike-like anchor pins secured to and extending from said plate, each pin having a head projecting from said plate in knob-like manner; and
    a driving and extracting instrument having a shank with an enlarged end and a pair of annular sector-shaped grooves of T-shaped cross-section in said end, each said groove being sized to slidably receive a head of a respective pin therein to connect said instrument to said bone implant.

5. The combination as set forth in claim 4 wherein each groove of said instrument has a circumferentially inclined base for wedging against a head of respective pin to fixedly connect said instrument to said agraffe.

6. The combination a set forth in claim 5 wherein each pin is threadably mounted in said plate.

7. The combination as set forth in claim 6 which further comprises at least one tack secured to and extending from said plate between said pins and of a length of at least one-third the length of said pins.

8. The combination as set forth in claim 4 comprising a plurality of pins of different lengths for detachable mounting in pairs in said plate.

9. A surgical agraffe for fixing artificial ligaments and tendons to a bone, said agraffe comprising
    a permanently deformable metal plate defining a connecting bridge element and a pair of projections extending from opposite sides of said bridge element, each projection including a threaded eyelet; and
    a pair of spike-like anchor pins, each said pin being threaded into and extending from an eyelet of a respective projection and including a head projecting from said respective projection in a knob-like manner.

* * * * *

UNITED STATES PATENT AND TRADEMARK OFFICE
CERTIFICATE OF CORRECTION

PATENT NO. : 4,793,335

DATED : December 27, 1988

INVENTOR(S) : Otto Frey, et al

It is certified that error appears in the above-identified patent and that said Letters Patent is hereby corrected as shown below:

```
Column 1, line 14 change "agraffe" to -agraffe or staple-
Column 1, line 47 cancel "or staple"
Column 3, line 7 change "now" to -not-
```

Signed and Sealed this

Nineteenth Day of September, 1989

Attest:

DONALD J. QUIGG

*Attesting Officer*   *Commissioner of Patents and Trademarks*